(12) United States Patent
Einarsson

(10) Patent No.: US 11,918,360 B1
(45) Date of Patent: Mar. 5, 2024

(54) SYSTEMS AND METHODS FOR EXAMINING HOLLOW ORGANS

(71) Applicant: The Brigham and Women's Hospital, Inc., Boston, MA (US)

(72) Inventor: Jon I. Einarsson, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 117 days.

(21) Appl. No.: 17/233,675

(22) Filed: Apr. 19, 2021

Related U.S. Application Data

(60) Provisional application No. 63/012,056, filed on Apr. 17, 2020.

(51) Int. Cl.
*A61B 5/20* (2006.01)
*A61B 5/00* (2006.01)
(Continued)

(52) U.S. Cl.
CPC ............ *A61B 5/202* (2013.01); *A61B 5/0084* (2013.01); *A61B 5/4839* (2013.01);
(Continued)

(58) Field of Classification Search
CPC ..... A61B 5/202; A61B 5/0084; A61B 5/4839; A61B 5/6853; A61B 5/6874;
(Continued)

(56) References Cited

U.S. PATENT DOCUMENTS 9,192,287 B2 11/2015 Saadat et al.
9,901,246 B2 2/2018 Whitmore, III
(Continued)

FOREIGN PATENT DOCUMENTS

CN 106309989 A 11/2017
WO 2013044182 A 3/2013
(Continued)

OTHER PUBLICATIONS

International Search Report dated Jun. 18, 2020 in Application No. PCT/US19/65723.
(Continued)

*Primary Examiner* — Brian T Gedeon
*Assistant Examiner* — Joshua Andrew Schum-Houck
(74) *Attorney, Agent, or Firm* — DeWitt LLP; Brian R. Pollack, Esq.

(57) ABSTRACT

The present disclosure provides diagnostic methods for evaluating a urinary bladder and methods of enhancing the visibility of the bladder from outside of a patient. The method includes introducing urinary catheter having a proximal end and a distal end into a patient's urinary bladder by way of the urethra, the urinary catheter including an outer tubular member including an inflatable balloon disposed thereon, and a visualization stylet that is slidably disposable within a passage defined in the outer tubular member. The method further includes inflating the inflatable member inside of the bladder, inflating the bladder with a liquid to enhance visualization of an inner surface of the bladder, illuminating a light source through the inflatable member to illuminate the inner surface of the bladder, and visualizing an inner portion of the bladder using the visualization stylet.

19 Claims, 1 Drawing Sheet

(51) Int. Cl.
*A61N 5/06* (2006.01)
*A61N 5/067* (2006.01)

(52) U.S. Cl.
CPC .......... *A61B 5/6853* (2013.01); *A61B 5/6874* (2013.01); *A61N 5/0601* (2013.01); *A61N 2005/061* (2013.01); *A61N 2005/0663* (2013.01); *A61N 5/067* (2021.08)

(58) Field of Classification Search
CPC .................. A61N 5/0601; A61N 5/067; A61N 2005/061; A61N 2005/0663
See application file for complete search history.

(56) References Cited

U.S. PATENT DOCUMENTS

| | | | | |
|---|---|---|---|---|
| 2008/0027416 A1* | 1/2008 | Hamel | ................. | A61B 5/0059 606/153 |
| 2008/0097468 A1 | 4/2008 | Adams et al. | | |
| 2009/0208143 A1* | 8/2009 | Yoon | ...................... | A61B 5/065 382/312 |
| 2009/0318798 A1* | 12/2009 | Singh | .................... | A61B 1/012 604/544 |
| 2016/0361120 A1* | 12/2016 | Brinkmann | .......... | A61B 18/245 |
| 2017/0258392 A1 | 9/2017 | Skieller et al. | | |

FOREIGN PATENT DOCUMENTS

| | | |
|---|---|---|
| WO | 2013071293 A1 | 5/2013 |
| WO | 2020123648 A1 | 6/2020 |

OTHER PUBLICATIONS

Written Opinion of the International Searching Authority dated Jun. 18, 2020 in Application No. PCT/US19/65723.

\* cited by examiner

SYSTEMS AND METHODS FOR EXAMINING HOLLOW ORGANS

CROSS-REFERENCE TO RELATED APPLICATIONS

The present patent application claims the benefit of priority to U.S. Patent Application Ser. No. 63/012,056, filed Apr. 17, 2020. The foregoing patent application is incorporated by reference herein in its entirety for all purposes.

BACKGROUND

A bladder catheter is routinely used during surgery for urinary bladder drainage. The traditional bladder catheter has an inflatable balloon at its distal end that is inflated after insertion in order to avoid spontaneous expulsion of the catheter during surgery. However, Applicant has noted that these devices and their associated methods of use have shortcomings. The present disclosure provides improvements over the state of the art, as set forth below.

SUMMARY OF THE DISCLOSURE

The purpose and advantages of embodiments of the present disclosure will be set forth in and become apparent from the description that follows. Additional advantages of embodiments of the present disclosure will be realized and attained by the methods and systems particularly pointed out in the written description and claims hereof, as well as from the appended drawings.

To achieve these and other advantages and in accordance with the purpose of the disclosure, as embodied herein, in accordance with one aspect, the disclosure provides a diagnostic method for evaluating a urinary bladder. The method includes introducing urinary catheter having a proximal end and a distal end into a patient's urinary bladder by way of the urethra, the urinary catheter including an outer tubular member including an inflatable balloon disposed thereon, and a visualization stylet that is slidably disposable within a passage defined in the outer tubular member. The method further includes inflating the inflatable member inside of the bladder, inflating the bladder with a liquid to enhance visualization of an inner surface of the bladder, illuminating a light source through the inflatable member to illuminate the inner surface of the bladder, and visualizing an inner portion of the bladder using the visualization stylet.

If desired, the method can further include performing a diagnostic procedure wherein the diagnostic procedure is performed ex-vivo after images have been collected of the bladder. If desired, the diagnostic procedure is performed in real time while the urinary catheter is inside the patient. The diagnostic procedure can include a cystoscopy. Alternatively, the diagnostic procedure can include continuous cystoscopy during a parallel procedure.

The method can further include performing a therapeutic procedure using the urinary catheter. The therapeutic procedure can include delivering a beneficial agent to a location inside the bladder or inside the ureter or kidney. The beneficial agent can include a medicament. The beneficial agent can include a therapeutic dose of light in a preselected wavelength band at a preselected intensity. The light includes laser light or incoherent light. In some implementations, the method can include fracturing a kidney stone using the laser light.

The method can further include detecting a bladder tumor by collecting images of an inner surface of the bladder, and comparing the images with a library of tissue samples. For example, the method can include detecting a carcinoma in situ lesion.

The disclosure further provides a diagnostic method for evaluating a urinary bladder that includes introducing a urinary catheter having a proximal end and a distal end into a patient's urinary bladder by way of the urethra. The urinary catheter includes an outer tubular member including an inflatable balloon disposed thereon, and a stylet that is slidably disposable within a passage defined in the outer tubular member. The method further includes inflating the inflatable member coupled to the urinary catheter insider of the bladder, inflating the bladder with a liquid to enhance visualization of an inner surface of the bladder, illuminating a light source through the inflatable member to illuminate the bladder, and visualizing an outer portion of the bladder from within the abdominal or pelvic cavity.

In some implementations, the light source can emit light in a red portion of the visible spectrum. In some implementations, the light source can be disposed inside of the inflatable balloon. In other implementations, the light source can be disposed on the stylet. Light can then be directed from the stylet, and through the inflatable balloon to illuminate the bladder. This can be very useful to help visualize and locate the bladder from outside of the bladder, such as with an endoscope by way of the abdominal cavity. If desired, the stylet can include a steerable distal tip region and an imaging device disposed at a distal tip thereof to receive images. The stylet can further include forward illumination to direct light through a distal end thereof, and a light source along a length of the stylet to illuminate the inflatable balloon. In further implementations, at least one of the stylet and the passage includes a lubricious coating along its length.

It is to be understood that both the foregoing general description and the following detailed description are exemplary and are intended to provide further explanation of the claimed embodiments. The accompanying drawings, which are incorporated in and constitute part of this specification, are included to illustrate and provide a further understanding of the methods and systems of the disclosure. Together with the description, the drawings serve to explain the principles of embodiments of the present disclosure.

DESCRIPTION

The purpose and advantages of embodiments of the present disclosure will be set forth in and become apparent from the description that follows. Additional advantages of embodiments of the present disclosure will be realized and attained by the methods and systems particularly pointed out in the written description and claims hereof, as well as from the appended drawings.

In gynecologic and urologic surgery, bladder injuries are fairly common with rates of 1-2% of cases. Cystoscopy is therefore advocated either routinely or selectively in pelvic surgeries in order to check bladder integrity at the end of surgery. Cystoscopy has been shown to add on average 17 minutes to surgical time during a hysterectomy and some gynecology providers are not familiar with the equipment needed to perform a cystoscopy. In addition, the limits of the bladder are not easily seen during pelvic surgery, and this is particularly important during a hysterectomy, since the bladder is in close vicinity to the uterus.

To achieve these and other advantages and in accordance with the purpose of the disclosure, as embodied herein, in accordance with one aspect, the disclosure provides systems and methods for cystoscopy.

In one illustrative implementation, a bladder catheter is provided that in turn includes a light source, such as a LED light disposed in a distal region of the bladder catheter, preferably inside of or near an inflatable member, or balloon. A CMOS chip can also be provided at or near the tip of the catheter in order to detect reflected light to facilitate the formation of images outside of the patient on a computer terminal.

Figure 1:
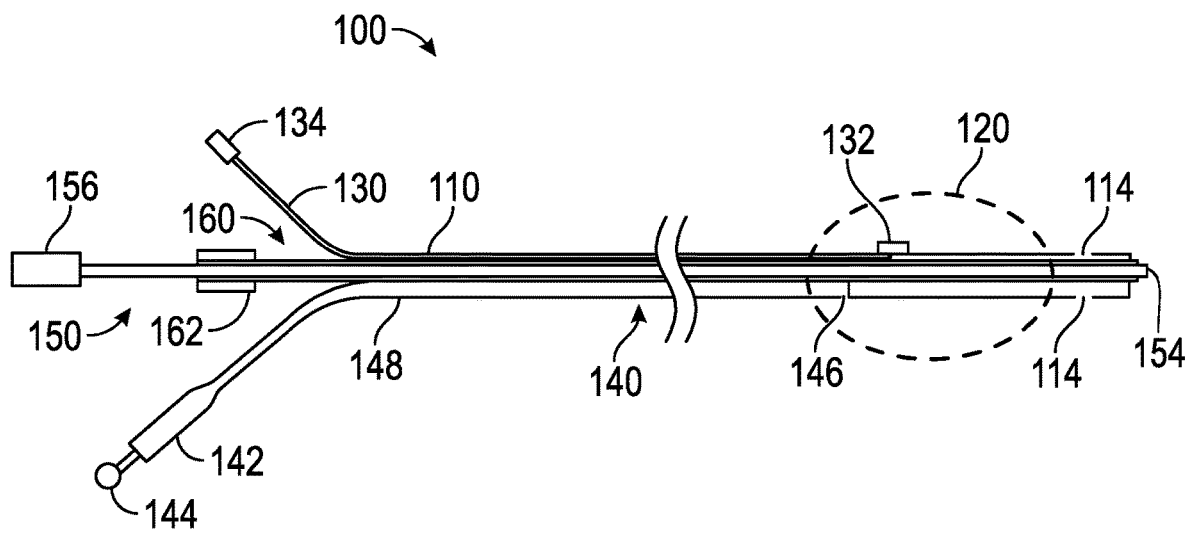
FIG. 1 is a schematic view of a device in accordance with the present disclosure.

For purposes of illustration, and not limitation, FIG. 1 illustrates a catheter device 100 configured for examination of the urinary bladder and nearby anatomic structures. The overall device 100 includes an outer catheter assembly that provides a main delivery vehicle for the overall system components. The outer catheter assembly includes an outer tubular member 110 having a proximal end and a distal end. The outer body 110 is typically disposable, and defines one or more (preferably three or four) elongate passages therethrough. One of these passages can permit passage of an inner viewing catheter assembly (150, 160), described in further detail below. Body 110 further includes an inflatable member, or balloon, 120 disposed about a distal portion thereof. The balloon is mounted about the periphery of tubular body 110, and includes an inflation circuit 140 that delivers inflation fluid, such as saline liquid, from a reservoir 142, through an inflation channel 148 and through an inflation port 146 into balloon 120 by actuating an actuator 144, such as a plunger or a syringe including the inflation fluid. The balloon is inflated in order to hold the system in place at the entry of the urinary bladder. The inflation channel 148 is preferably a dedicated passage along the length of outer body 110.

As further illustrated in FIG. 1, body 110 can define therein evacuation ports 114 to permit urine or other fluid introduced into the bladder to be removed from the bladder through a dedicated channel defined through body 110. While the ports 114 can similarly be used to inflate the bladder with saline, for example, in order to provide an enlarged volume for examination of the anatomy by the device 100, it is preferred that saline be delivered through a separate passage defined along the body 110.

Device 100 can further include an illumination circuit 130 that in turn includes a lighting device such as a LED chip 132, or a LED array, as desired, disposed inside or proximate the balloon or inflatable member 120. The LED chip 132 can be coupled via an electrical conductor to an electrical connector 134 to couple the LED chip to an electrical power supply. It will be appreciated that while a LED chip and electrical circuit is preferred, it is also possible to deliver light through the circuit if a fiber optic cable is used in lieu of an electrical circuit that conducts light generated outside the catheter from a light source to a location inside or near the balloon. The LED chip or array can be configured to deliver light in any desired wavelength band. For example, the LED chip or array can be configured to be tuned to a desired wavelength range, and can be adjustable to provide wavelengths from the infrared to the ultraviolet. Preferably, the LED chip or array is able to deliver light in a red visible wavelength range at around 675-725 nm wavelength. It is also possible to instead include the LED chip or array on the inner stylet or viewing assembly 150, 160, described below.

The inner viewing catheter assembly 150, 160 is slidably disposed within a passage defined by body 110, or within a discrete passage of body 110 if body 110 is a multi-passage extrusion. Preferably, one or both of assembly 150, 160 and the corresponding passage of 110 includes a lubricious coating to permit low friction passage of the inner assembly 150, 160. The inner assembly 150, 160 can be provided as a single unit wherein a stylet as described below is surrounded by a steering sheath 160. Alternatively, and as illustrated, the inner viewing catheter assembly 150, 160 can be comprised of an inner visualization stylet 150 that is in turn slidably disposed within an outer sheath 160. As illustrated, outer sheath 160 includes a proximal end, a distal end, and defines an elongate passage along its length. An actuator handle, represented schematically by 162, can be provided, and this can be pulled or pushed with respect to body 110 to advance the viewing catheter assembly into the bladder and, if desired, into one of the patient's ureters. The inner portion 150 of the assembly can include a visualization stylet that includes a CMOS photodetector chip 154 disposed at a distal end thereof that can be exposed to the surrounding environment, or located underneath a viewing lens. The CMOS chip can be surrounded by a light conducting fiber bundle that can be used to provide forward illumination, if desired, in the event that the LED chip 132 does not provide sufficient illumination. The inner portion 150 of the assembly includes an elongate body to permit passage of an electrical conductor to electrically couple the CMOS chip to an electrical coupling 156, that can then direct detected signals to a computer and a viewing screen to permit a user to view activity in real time.

In one implementation, the distal region of the inner portion of the assembly can be biased to bend in a preselected direction (i.e., to curl in a desired direction) when unconstrained. This can help effectuate steering of the inner assembly 150, 160 by advancing the distal region of the inner assembly 150 out of the distal tip of the sheath portion 160 to permit it to bend in a selected direction. The assembly 150, 160 can then be advanced in the new direction to permit viewing of internal structure of the bladder, or to advance the assembly 150, 160 into a ureter to examine the ureter or upstream anatomy, as desired.

Alternatively, and as alluded to above, sheath 160 can be replaced, for example, with a steering catheter that houses style 150. Or, 150 and 160 can be integrated such that the visualization stylet includes a steering mechanism composed of one, two, or more pull wires. Moreover, in addition to illuminating the bladder, a steering catheter including an inner assembly 150 including a visualization stylet can also be directed from outside the patient through the vagina, uterus, and fallopian tube into the abdominal cavity without puncturing a tissue structure to view the illuminated bladder illuminated by catheter 100, although the present disclosure does not exclude puncturing tissue structures.

As mentioned above, the inner assembly 150, 160 can be an integrated assembly including a viewing CMOS chip. Forward illumination can also be provided by surrounding the CMOS chip, which is typically a 1 mm square with light conducting fiber bundles in the space between the chip and the circular periphery of the assembly 150, 160, wherein the fibers or fiber bundles are coupled to a light source outside of the patient, or within the assembly 150, 160. Moreover, LED chip or array 132 can be omitted from the outer catheter, and can instead be provided a predetermined distance from the distal end of the assembly 150, 160, wherein the LED chip or array can shine through the outer catheter and balloon to illuminate the bladder. To facilitate this, the outer catheter including the tubular member 110 and balloon 120 can be formed at least in part from light transmissive material. The inner assembly 150, 160 can thus be a reusable element, and the sheath including the tubular member 110 and balloon 120 can be disposable.

Figure 2:
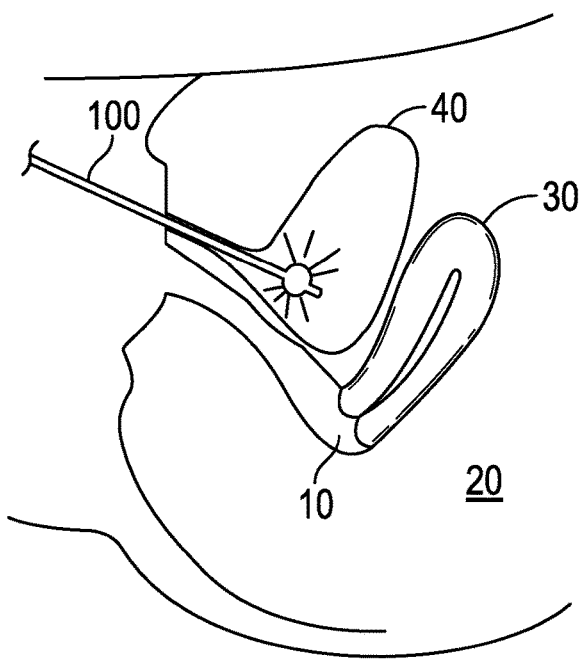
FIG. 2 is a schematic view of use of the device of FIG. 1 in a patient.

In further implementations of a method, and with reference to FIG. 2, the catheter 100 can be placed in the bladder of a patient and the inflatable member 120 can be inflated to hold the catheter in place. At this time, any urine in the bladder can be evacuated via ports 114, and the bladder can be at least partially inflated, if desired, with saline via catheter 100. The light source (e.g., 132, or a light source on the inner assembly 150, 160) can then be turned on, such as by way of a switch on the catheter or on a computer terminal that is operably coupled to the catheter, such as by a data cable or by way of a wireless communication connection. In some implementations, a LED light source can be used as illustrated. A LED light source can be advantageous as it generates very little heat and will not cause a thermal injury. In addition, when disposed inside of the inflatable member (e.g., 120), or inside of the catheter and radiating through the balloon, any heat output by the LED can be absorbed and dissipated by inflation fluid disposed in the inflatable member. The LED light can then illuminate the bladder and this will in turn enable the surgeon to better view the limits of the bladder and the distance from the bladder and other organs including the uterus when maneuvering in the abdominal catheter with one or more different instruments. It is particularly helpful to illuminate the bladder from the inside, so that a surgeon performing a procedure in the abdominal and/or pelvic cavity does not get too close to the bladder which could otherwise potentially result in damaging the bladder.

In some implementations, diagnosis can be conducted in real time, such as by examining tissue inside the urinary tract using device 100, and/or using an endoscope to view the inflated, illuminated bladder from the outside. In other implementations, video can be recorded and reviewed later by a physician or analyzed on a computer. In some further implementations, analyzing image data on a computer can include applying an algorithm to the image data to facilitate a diagnosis. In some implementations, disclosed methods can further include examining at least one anatomical structure, such as the urinary bladder, for at least one abnormality such as a lesion.

As mentioned above, in some implementations, the LED can include an LED array including arrays of different colors and wavelengths to generate different color temperatures and light wavelength distributions. But, by way of further example, visible light and/or ultraviolet or infrared light can be generated and transmitted into the tissue in order to facilitate a diagnostic result and/or a therapeutic result. For purposes of enhanced viewing of the bladder from the outside, red light has found to be particularly useful.

Devices and methods in accordance with the disclosure can also be useful during laparoscopic and robotic procedures, which currently amount to the majority of cases performed in pelvic surgery. The bladder illumination created using devices in accordance with the present disclosure can be seen laparoscopically/robotically in a similar fashion as a light inside of a tent will be seen from the outside and it has the potential to decrease the risk of bladder injury during pelvic surgery due to the enhanced visibility of the bladder arising from the illumination.

In some implementations, for example, the CMOS chip 154 can include a 1 mm CMOS chip, or smaller, and this can be placed on the tip of the inner assembly 150/160. The CMOS chip can then be connected by conductive leads to an external adapter that in turn connects to a monitor, for example, via a standard HDMI connector. The light from the LED light can continuously illuminate the bladder and this therefore enables continuous cystoscopy during the surgical procedure if the surgeon so desires. It also permits, in some implementations, a quick cystoscopy at the end of the case since the catheter is already in place. The disclosed embodiments can be expected to save time over conventional cystoscopy and it will make it simpler for providers to perform.

A further illustrative method in accordance with the disclosure includes introducing a urinary catheter having a proximal end and a distal end toward a patient's urinary bladder by way of the urethra, advancing the distal end of the catheter into the urinary bladder, and inflating an inflatable member near the distal end of the catheter to hold the urinary catheter in place. The urinary catheter defines a channel along its length in some implementations to permit urine to pass through the catheter to evacuate the bladder and to permit saline to be introduced into the bladder to inflate the bladder to facilitate viewing of the bladder from the inside. Illustrative structures for performing this are provided in FIG. 1, wherein urine can be evacuated by way of ports 114, which can be coupled to a discrete evacuation channel through body 110, or it is also possible to evacuate urine and introduce saline through the main passage of the body 110 along an annular space defined between the body of sheath 160 and the inner surface of the passage in which it resides.

In some embodiments, the disclosed methods can further include directing signals from the processor to a display screen. In some embodiments, the method can include directing a laser light signal through the urinary catheter to treat tissue inside of the patient, such as by irradiating the inner wall of the urinary bladder or other structure with laser light. In some embodiments, the diagnostic method can be repeated a plurality times over a plurality of examinations in order to track progress of a treatment regimen of the patient.

The disclosed urinary catheters can be provided with a hydrophobic coating along all or a part of its length, such as by shrinking a thin walled hydrophobic (e.g., PTFE, PVDF or another fluoropolymer) sleeve around its periphery. If desired, the urinary catheter can be coated with a hydrophilic coating along all or part of its length (e.g., polyvinylpyrrolidone "PVP" or other suitable material). If desired, any catheter herein can be provided with a coating of a lubricant along all or a portion of its length, such as silicone oil and the like.

The methods and devices provided by the present disclosure, as described above and shown in the drawings, provide for methods and systems for medical diagnosis and treatment with superior properties as described herein. It will be apparent to those skilled in the art that various modifications and variations can be made in the embodiments of the present disclosure described herein without departing from the spirit or scope of the disclosure. Thus, it is intended that the present disclosure include modifications and variations that are within the scope of the appended claims and their equivalents.

What is claimed is:

1. A diagnostic method for evaluating a urinary bladder, comprising:

introducing a urinary catheter having a proximal end and a distal end into a patient's urinary bladder by way of the urethra, the urinary catheter including an outer tubular member including an inflatable member disposed thereon, and a stylet that is slidably disposable within a passage defined in the outer tubular member;

inflating the inflatable member inside of the bladder;

inflating the bladder with a liquid to enhance visualization of an inner surface of the bladder;

illuminating a red-light source through the inflatable member to illuminate the bladder; and directly visualizing an outer portion of the illuminated bladder from within the abdominal or pelvic cavity using a separate visualization device situated in the abdominal or pelvic cavity.

2. The method of claim 1, wherein the red-light source is disposed inside of the inflatable member.

3. The method of claim 2, wherein the red-light source is disposed on the stylet, and further wherein light is directed from the stylet, and through the inflatable member.

4. The method of claim 1, wherein the stylet includes a steerable distal tip region and an imaging device disposed at a distal tip thereof to receive images.

5. The method of claim 4, wherein the stylet further includes forward illumination to direct light through a distal end thereof, and further wherein the red-light source is arranged along a length of the stylet to illuminate the inflatable member.

6. The method of claim 1, wherein at least one of the stylet and the passage includes a lubricious coating along its length.

7. The method of claim 1, wherein the red-light source is configured to deliver light in a red visible wavelength range between 675 nm and 725 nm in wavelength.

8. The method of claim 1, further comprising performing a diagnostic procedure wherein the diagnostic procedure is performed ex-vivo after images have been collected of the bladder.

9. The method of claim 8, wherein the diagnostic procedure is performed in real time while the urinary catheter is inside the patient.

10. The method of claim 8, wherein the diagnostic procedure includes a cystoscopy.

11. The method of claim 8, wherein the diagnostic procedure includes continuous cystoscopy during a parallel procedure.

12. The method of claim 1, further comprising performing a therapeutic procedure using the urinary catheter.

13. The method of claim 12, wherein the therapeutic procedure includes delivering a beneficial agent to a location inside the bladder or inside the ureter or kidney.

14. The method of claim 13, wherein the beneficial agent includes a medicament.

15. The method of claim 13, wherein the beneficial agent includes a therapeutic dose of light in a preselected wavelength band at a preselected intensity.

16. The method of claim 15, wherein the light includes laser light.

17. The method of claim 16, wherein the laser light is used to fracture a kidney stone.

18. The method of claim 1, further comprising detecting a bladder tumor by collecting images of an inner surface of the bladder, and comparing the images with a library of tissue samples.

19. The method of claim 1, further comprising detecting a carcinoma in situ lesion.

* * * * *